US008532741B2

(12) United States Patent
Heruth et al.

(10) Patent No.: US 8,532,741 B2
(45) Date of Patent: Sep. 10, 2013

(54) METHOD AND APPARATUS TO OPTIMIZE ELECTRODE PLACEMENT FOR NEUROLOGICAL STIMULATION

(75) Inventors: Kenneth T. Heruth, Edina, MN (US); Gabriela C. Miyazawa, New Brighton, MN (US); Paul W. Wacnik, Minneapolis, MN (US); Gregory F. Molnar, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1193 days.

(21) Appl. No.: 11/683,695

(22) Filed: Mar. 8, 2007

(65) Prior Publication Data

US 2008/0064947 A1 Mar. 13, 2008

Related U.S. Application Data

(60) Provisional application No. 60/843,476, filed on Sep. 8, 2006.

(51) Int. Cl.
*A61B 5/055* (2006.01)
*A61N 1/18* (2006.01)

(52) U.S. Cl.
USPC .............................. 600/424; 600/411; 607/45

(58) Field of Classification Search
None
See application file for complete search history.

(56) References Cited

U.S. PATENT DOCUMENTS

| 5,437,277 | A | * | 8/1995 | Dumoulin et al. | 600/424 |
|---|---|---|---|---|---|
| 5,592,939 | A | | 1/1997 | Martinelli | |
| 5,740,808 | A | | 4/1998 | Panescu et al. | |
| 5,913,820 | A | | 6/1999 | Bladen et al. | |
| 5,983,126 | A | | 11/1999 | Wittkampf et al. | |
| 6,061,587 | A | * | 5/2000 | Kucharczyk et al. | 600/411 |
| 6,227,203 | B1 | | 5/2001 | Rise et al. | |
| 6,381,485 | B1 | | 4/2002 | Hunter et al. | |
| 6,474,341 | B1 | | 11/2002 | Hunter et al. | |
| 6,482,182 | B1 | | 11/2002 | Carroll et al. | |
| 6,493,573 | B1 | | 12/2002 | Martinelli et al. | |
| 6,516,212 | B1 | | 2/2003 | Bladen et al. | |
| 6,526,305 | B1 | | 2/2003 | Mori | |
| 6,990,377 | B2 | | 1/2006 | Gliner et al. | |
| 7,217,276 | B2 | | 5/2007 | Henderson et al. | |
| 7,346,382 | B2 | * | 3/2008 | McIntyre et al. | 600/407 |
| 7,471,974 | B2 | * | 12/2008 | Hartlep et al. | 600/424 |

(Continued)

FOREIGN PATENT DOCUMENTS

| EP | 1319368 | 6/2003 |
|---|---|---|
| EP | 1398641 | 3/2004 |
| EP | 1629789 | 3/2006 |
| WO | WO-2006/017053 | 2/2006 |

OTHER PUBLICATIONS

International Search Report and Written Opinion for PCT/US2007/010072 mailed Jan. 2, 2008 claiming benefit of U.S. Appl. No. 11/683,695.

(Continued)

*Primary Examiner* — Long V. Le
*Assistant Examiner* — Angela M Hoffa
(74) *Attorney, Agent, or Firm* — Harness, Dickey & Pierce, PLC

(57) ABSTRACT

A method and apparatus can be used to guide or navigate an instrument relative to a body. Various types of information can be used to assist in the navigation, such as MRI data, diffusion tensor image data, and the like. The information can assist in identifying the portions of the body.

30 Claims, 7 Drawing Sheets

(56) References Cited

U.S. PATENT DOCUMENTS

| | | | |
|---|---|---|---|
| 7,505,806 B2 * | 3/2009 | Masutani et al. | 600/410 |
| 7,860,548 B2 * | 12/2010 | McIntyre et al. | 600/407 |
| 7,904,134 B2 * | 3/2011 | McIntyre et al. | 600/407 |
| 8,180,601 B2 * | 5/2012 | Butson et al. | 703/2 |
| 2002/0198572 A1 | 12/2002 | Weiner | |
| 2003/0114752 A1 | 6/2003 | Henderson et al. | |
| 2003/0234781 A1 | 12/2003 | Laidlaw et al. | |
| 2004/0138550 A1 * | 7/2004 | Hartlep et al. | 600/407 |
| 2004/0215071 A1 | 10/2004 | Frank et al. | |
| 2005/0049486 A1 | 3/2005 | Urquhart et al. | |
| 2005/0085714 A1 | 4/2005 | Foley et al. | |
| 2005/0085720 A1 | 4/2005 | Jascob et al. | |
| 2005/0277995 A1 | 12/2005 | Gill | |
| 2005/0281385 A1 | 12/2005 | Johnson et al. | |
| 2006/0017749 A1 | 1/2006 | McIntyre et al. | |
| 2006/0084867 A1 | 4/2006 | Tremblay et al. | |
| 2006/0093583 A1 | 5/2006 | Hartlep et al. | |
| 2007/0179558 A1 * | 8/2007 | Gliner et al. | 607/45 |

OTHER PUBLICATIONS

"Diffusion Tensor Imaging" as copied from http://en.wikipedia.org/wiki/diffusion_tensor_imaging—Wikipedia, the free encyclopedia on Sep. 6, 2006 (1 sheet).

"Fiber Tract Following in the Human Brain Using DT-MRI Data," Basser, et al.. IEICE Trans. Inf. & Syst., vol. E85-D, No. 1 Jan. 2002, pp. 15-21.

"Diffusion Tensor Imaging: Concepts and Applications", Bihan, et al., Journal of Magnetic Resonance Imaging 13:534-546 (2001).

Subthalamic Nucleus Deep Brain Stimulation: Accurate Axonal Threshold Prediction with Diffusion Tensor Based Electric Field Models, Chaturvedi, et al. 28th IEEE EMBS Annual International Conference, Aug. 30-Sep. 3, 2006, New York City, New York, USA. (4 sheets).

"A Primer on Diffusion Tensor Imaging of Anatomical Substructures," DaSilva, et al., NeuroSurg. Focus / vol. 15 / Jul. 2003. Published by the Journal of Neurosurgery and American Association of Neurological Surgeons, Jul. 2003, vol. 15, Issue.

"Diffusion Tensor and Functional MRI Fusion with Anatomical MRI for Image-Guided Neurosurgery," Talos, et al. R.E. Ellis and T.M. Peters (Eds.): MICCAI 2003, LNCS 2878, pp. 407-415, 2003. Copyright Springer-Verlag Berlin Heidelberg 2003.

"Visualization Software Helps Researchers Help Parkinson's Disease Patients," McIntyre, et al. http://www.reedlink.com/SingleArticle~ContentId~55628~pub~PD.html. Viewed and downloaded Sep. 6, 2006.

"Regularization of Diffusion-Based Direction Maps for the Tracking of Brain White Matter Fascicles," Poupon, et al. NeuroImage 12, 184-195 (copyright 2000 by Academic Press).

"Virtual in Vivo Interactive Dissection of White Matter Fasciculi in the Human Brain," Catani, et al. NeuroImage 17, 17-94 (copyright 2002 Elsevier Science (USA).

"Atlas for Stereotaxy of the Human Brain, with an Accompanying Guide," Schaltenbrand, et al., Second, Revised and Enlarged Edition 1977, includes cover page, plate 39, and plate 25.

"Correlative Anatomy of the Nervous System," Crosby, E.C., et al., Macmillan, p. 57, 1962. (1 sheet).

"Correlative Anatomy of the Nervous System," Crosby, et al. Macmillan, p. 88. 1962. (1 sheet).

* cited by examiner

METHOD AND APPARATUS TO OPTIMIZE ELECTRODE PLACEMENT FOR NEUROLOGICAL STIMULATION

CROSS-REFERENCE TO RELATED APPLICATIONS

This application claims the benefit of U.S. Provisional Application No. 60/843,476, filed on Sep. 8, 2006. The disclosure of the above application is incorporated herein by reference.

FIELD

The present teachings relate to a surgical procedure, and particularly to a computer assisted surgical procedure for determining an anatomical location with various imaging techniques.

BACKGROUND

The statements in this section merely provide background information related to the present disclosure and may not constitute prior art.

Surgical procedures are often performed by skilled individuals, such as surgeons. The surgeons can perform various surgical procedures based upon their training and past experience, augmented by study of a particular patient. Nevertheless, various portions of a particular patient may be difficult to examine or identify depending upon the area of the anatomy to be examined and the positioning of the patient.

Surgical procedures where these difficulties may arise can include various neurosurgical procedures that affect various functions of the brain and nervous system. For example, a tumor or growth may be selected to be removed from a brain or a portion of the spinal column or the nervous system may be stimulated. Other procedures, however, may be performed to augment a portion of the brain without removing a portion of the brain, affecting surrounding tissue in the brain, or without visual cues of differences between the area of the brain to be affected and surrounding areas.

For example, certain neurological procedures can be performed that affect "functional targets". The functional targets can be portions of the brain that naturally affect or control various portions of the anatomy but are, for various reasons, damaged. These functional targets in the brain can be stimulated through procedures such as deep brain stimulation (DBS). Functional targets, even if malfunctioning in a particular manner, may not differ anatomically or visually from the surrounding tissues. Functional targets can also be found in other portions of an anatomy, such as a spinal cord, peripheral nerves, etc. Therefore, it is desirable to provide a system that is able to determine the position of a functional target in the brain.

SUMMARY

A computer assisted surgical system or navigation system can be used to determine a portion of anatomy, such as a portion in a brain or a nervous system that may not be visually distinct from surrounding tissue portions. It will be understood that although a system can determine a particular region of a brain, it can also be used to determine a position of other portions of the anatomy. In one example, various imaging techniques, such as magnetic resonance imaging (MRI) can be used to obtain a detailed image of the brain. Also, additional information or data can be collected such as diffusion tensor data regarding a selected portion of the anatomy. A diffusion tensor can be generated from the diffusion data that describes or identifies the three dimensional shape of diffusion of a material in the diffusion data.

A tensor can be created to manipulate the various diffusion data obtained with the imaging system, such as a magnetic resonance imaging system. The data can be used to measure the flow of water or diffusion of water as measured in the image data. The image data can be analyzed to determine the greatest direction of diffusion of water as measured in the image data. The tensor of the data can be used to assist in determining the greatest vector of diffusion.

Multiple voxels of other image data portions can be analyzed to measure a direction of diffusion. After multiple voxels have been analyzed a determination of a direction and connection of a flow of water can be determined. This connection can be used to assist in identifying anatomical regions, such as fiber tracts. The connected regions can be overlaid on other image data, such as MRI image data for reference.

A system is provided that can determine various anatomical or functional targets based upon landmarks in the brain or additional data that can be used to determine certain or selected anatomical structures. The system can plan a route or trajectory to reach the selected anatomical targets and determine a point of entry to reach the anatomical target. The system can be fully automatic and include a processor to execute instructions to determine the anatomical targets. The system can also be used to navigate an instrument to a selected region, which may include the function targets. The system can also be combined with manual inputs. The anatomical target can include a functional target which can be a portion of the brain or nervous system that controls a certain function of or transmits a signal to the anatomy. Although it will be understood that a similar system can be used to obtain access or determine a position of a tumor, a damaged region of the brain, portions of the brain based upon an anatomical landmarks, or other portions of the anatomy.

A system can be used to identify selected regions of the anatomy, such as portions in the brain or other parts of the nervous system. For example, diffusion imaging that can include diffusion tenser imaging data and can be used to assist in identifying fiber tracts in an anatomical body. For example, diffusion tenser imaging (DTI) can be used to identify neurons, and in particular, to identify an axon and dendrites. While the neuron can include a cell body, a region of the anatomy can include a plurality of cell bodies with various axons and dendrites relative thereto. As is understood in the art, stimulation of selection portions of the anatomy, such as neurons, can provide selected results. However, providing stimulation of a particular portion of the neuron, such as the axon, can increase the efficiency and preciseness of a selected procedure with reduced side effects to adjoining tissue. Therefore, the DTI data can provide a greater clarity of a particular axon for stimulation thereof, according to various embodiments. The DTI data can assist in navigation or assist in identifying a region of anatomy relative to which an instrument can be navigated to perform a selected procedure.

According to various embodiments a surgical navigation system to navigate a procedure on a patient is disclosed. The system can include an imaging device operable to obtain diffusion data within the patient and a tracking system including a localizer and a tracking device operable to be tracked by the tracking system. An instrument can be associated with the tracking device. A processor can be used to determine a selected region of the patient and a relative position of the instrument to the patient and the image data including the selected region of the patient.

According to various embodiments, a method of performing a procedure on a selected portion of an anatomy is disclosed. The method can include obtaining image data of the selected portion of the anatomy and obtaining a second source of data relating to the selected portion of the anatomy. The method can also include analyzing the second source of data and identifying a fiber tract in the obtained image data at least in part with the analyses of the second source of data. A selected position of treatment in the anatomy can be determined and a treatment can be applied to the selected position in of the anatomy.

According to various embodiments a method for performing a surgical procedure on an anatomy is disclosed. The method can include obtaining data regarding the anatomy and analyzing the obtained data. A fiber tract in the anatomy can be determined based upon the analyzed obtained data. A region of the anatomy can also be identified relative to the identified fiber tract. An instrument can be navigated relative to the anatomy via the identified fiber tract and a therapy can be applied to the identified fiber tract, the identified region, or combinations thereof.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 5:
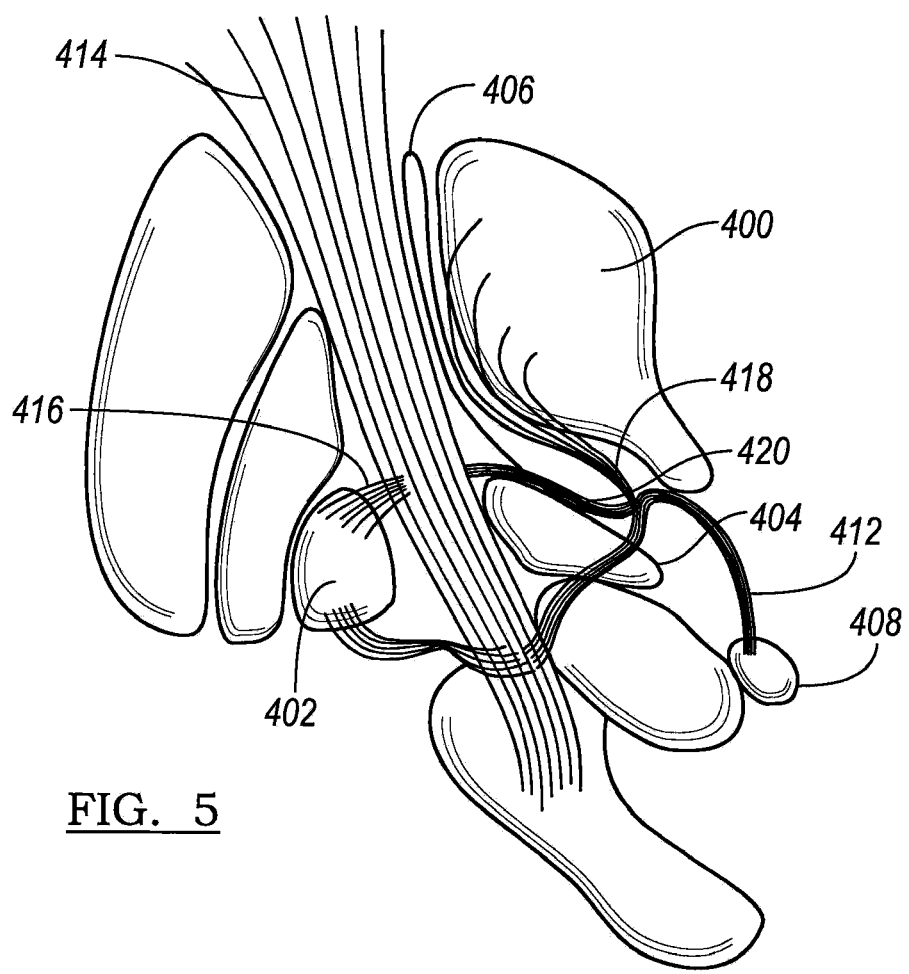
Figure 6:
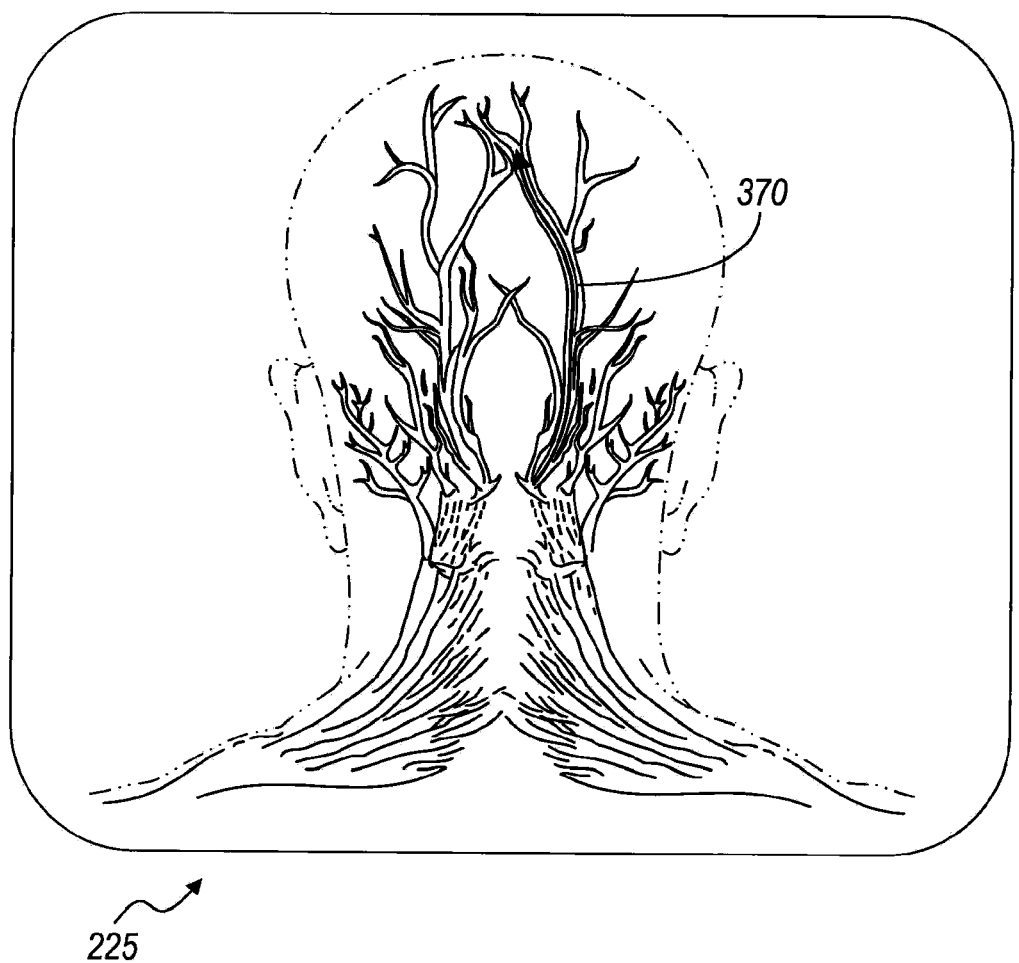

FIG. 5 schematically illustrates portions of a brain and connections or fiber tracts between the portions; and FIG. 6 schematically illustrates peripheral occipital nerve tracts.

DETAILED DESCRIPTION OF VARIOUS EMBODIMENTS

The following description is merely exemplary in nature and is not intended to limit the present disclosure, application, or uses. Though the following teachings relate to a method and apparatus for use with a neurosurgical procedure, this is merely exemplary and not intended to limit the scope of the present disclosure.

Identifying various structures of an anatomy, such as portions of the neuroanatomy, can be useful for performing selected procedures on a brain, such as deep brain stimulation (DBS), ablation, tumor removal, drug delivery, gene therapy, cell delivery therapy, needle delivery, implant delivery, lead or electrode delivery, and the like. The identification of various brain structures can be difficult based on the location, size, activity, and other factors. For example, identifying the location of the sub-thalamic nucleus (STN) or basal ganglia can be difficult based upon its location within the brain and its visual similarity to the area surrounding it. In addition determining the tracts or fiber connections between different regions, in the brain or otherwise, can also be difficult.

It is also useful to identify portions of the anatomy outside of the brain. Tracts or pathways exist throughout an anatomy. For example, grey and white matter in a spinal column, peripheral nerve tracts or bundles, or combinations of these. The tracts can be identified, as discussed herein, for various treatment purposes.

According to the present teachings various imaging techniques can be used to identify discrete areas of the anatomy, such as neurons and axons in the brain. Thus, treatments can be applied to the STN or selected axons of selected neurons to treat a disease, such as Parkinson's, epilepsy, or psychiatric disorders. Treatments can include ablation, radio seed placement, short term or long term electrical or thermal stimulation, etc.

In addition to providing a therapy (e.g. stimulation) to selected regions of a brain, such as the fibers or tracts, therapies can be provided to other portions of the anatomy. For example, therapies can be provided to selected portions of neurons, such as an axon, of spinal column neurons. Neurons located in the dorsal column can be stimulated for various purposes. Briefly, stimulation of neurons in the dorsal column can be used to alleviate or reduce pain.

Stimulation of a selected axon or fiber tract, as discussed herein, can allow for increased efficiency in using stimulation for pain relief and can assist in reducing various side effects. For example, identifying a particular axon to be stimulated can reduce side effects by eliminating or shielding non-selected axons from stimulation. Therefore, side effects to a patient can be substantially eliminated or reduced by providing stimulation to only a selected axon. It will be understood that the DTI processing can assist in determining and identifying particular axons. Further, the DTI processing can be used in conjunction with image data, including magnetic resonance image data, to assist in identifying particular axons to be stimulated.

As discussed further herein, the identification of selected axons can be used in conjunction with a navigation system 200 to assist in determining a position of an instrument 252 relative to the determined and/or selected axon. Therefore, the navigation system 200 can assist in positioning the instrument 252 relative to the selected axon according to various imaging and tracking techniques and systems, discussed herein. Due to the combination of the determination of a selected axon and navigation of the instrument 252 relative to the selected axon substantially precise positioning and treatment can be provided.

As discussed herein, identifying one or a bundle of tracts can be used to specifically provide treatment. That is, rather than navigating an instrument to a general area of interest, the instrument can be navigated to a specific and localized position. For example, the instrument can be navigated near a specific tract or bundle to provide treatment substantially to that tract or bundle. One skilled in the art, however, will understand that the instrument 252 can be navigated to any selected location.

Figure 1:
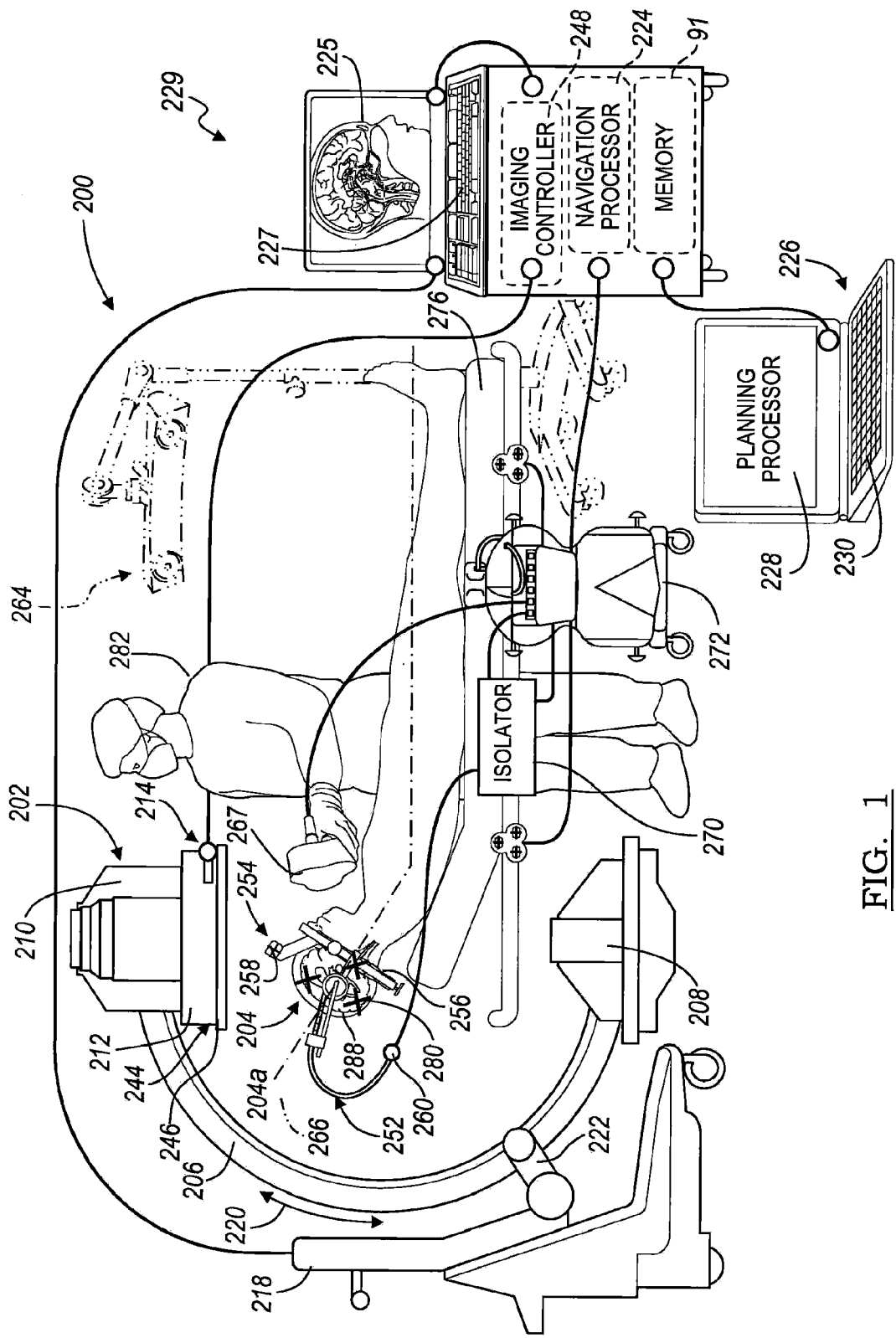
FIG. 1 illustrates a diagram of a surgical navigation system according to various embodiments.

An exemplary system that can be used to perform a guided procedure can include the navigation system 200, in FIG. 1. The navigation system can be used for various procedures to stimulate a selected portion of the anatomy. The navigation system 200 can include the navigation processor 224 and a planning processor 226 that can execute instructions to perform at least portions of a guided procedure using selected information. The navigation system 200 can also be used to track the location of the instrument 252, such as a deep brain stimulator or appropriate stimulator, relative to a patient 204 to assist in the implementation a guided procedure. The planning processor 226 can assist in this and can be used to create or determine a plan for the procedure.

It should further be noted that the navigation system 200 may be used to navigate or track the instrument 252, which can include catheters, probes, needles, guidewires, instruments, implants, deep brain stimulators, electrical leads, etc. Moreover, the instrument 252 can be used in any region of the body. The navigation system 200 and various instruments 252 may be used in any appropriate procedure, such as one that is generally minimally invasive, arthroscopic, percutaneous, stereotactic, or an open procedure. An exemplary navigation system 200 can also include an imaging device 202. One skilled in the art will understand that the discussion of the imaging device 202 is merely for clarity of the present discussion and any appropriate imaging system, navigation system, patient specific data, and non-patient specific data can be used. For example, the imaging device can be a magnetic resonance imager that can also be used to collect diffusion data. Also, the navigation system 200 may not have an imaging system, but may simply have access to image data or may be an imageless system.

The navigation system 200 can include the optional imaging device 202 that is used to acquire pre-, intra-, or post-operative or real-time image data of a patient 204. Although any appropriate imaging system can be used to collect or obtain image data at any appropriate time. The image data acquired with the imaging device 204 can be used to assist in determining the anatomical or functional targets and the trajectories. The illustrated imaging device 202 can be, for example, a fluoroscopic x-ray imaging device that may be configured as a C-arm 206 having an x-ray source 208, an x-ray receiving section 210. Image data may also be acquired using other imaging devices, such as those discussed herein. An example of a fluoroscopic C-arm x-ray device that may be used as the optional imaging device 202 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

The imaging system, however, may also include MRI systems. MRI systems can be used to collect image data that includes diffusion of water data between a series of image data. The MRI can include intraoperative systems such as the POLESTAR™ N20 sold by Medtronic Navigation, Inc., of Colorado, USA. Therefore, the imaging device 202 can be any appropriate device or system.

An optional imaging device controller 218 may control the imaging device 202, such as the C-arm 206, to capture the x-ray images received at the receiving section 210 and store the images for later use. The controller 218 may also be separate from the C-arm 206 and/or control the rotation of the C-arm 206. For example, the C-arm 206 can move in the direction of arrow 220 or rotate about a longitudinal axis 204a of the patient 204, allowing anterior or lateral views of the patient 204 to be imaged. Each of these movements involves rotation about a mechanical axis 222 of the C-arm 206.

Image data of any appropriate type, such as image data obtained or collected with the C-arm can be forwarded, to a navigation computer and/or processor 224 having a display 225 and a user interface 227. The navigation processor 224, display 225, and user input interface 227 can be part of a work station 229. The navigation processor 224 can include a planning processor, as discussed herein, or the separate planning processor system 226 can be included. The planning processor system 226 can also include a display 228 and a user input 230. It will also be understood that the image data can be, but is not necessarily, first retained in the controller 218, but may be directly transmitted to the workstation 229 or the planning processor system 226.

While the optional imaging device 202 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 204. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions," which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites or functional targets within the patient 204. It should further be noted that the optional imaging device 202, as shown in FIG. 1, provides a virtual bi-plane image using a single-head C-arm fluoroscope as the optional imaging device 202 by simply rotating the C-arm 206 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulation leads, electrical leads, needles, implants, probes, or other instrument, introduced and advanced in the patient 204, may be superimposed in more than one view on display 225 or 228 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomical and functional information from the image data. MRI image data can be registered and compensated for motion correction, using dynamic reference frames (DRF) discussed further herein. Also, different types of MRI techniques can be used to more clearly illustrate different portions of the anatomy. As discussed above, T1 weighted MRI images may be used to display selected anatomical regions in the brain. Further, MRI systems can be used to obtain diffusion image data, of a selected region of the patient 204, and tensor and tensor analysis can be performed to obtain diffusion tensor image (DTI) data.

With continuing reference to FIG. 1, the navigation system 200 can further include an electromagnetic navigation or tracking system 244 that includes a localizer, such as a transmitter coil array 246, a coil array controller 248, a navigation probe interface 272, the instrument 252 (e.g. catheter, needle, or instruments, as discussed herein) and a dynamic reference frame 254. The dynamic reference frame 254 can include a dynamic reference frame member or holder 256 and a removable tracking device 258. Alternatively, the dynamic reference frame 254 can include a tracking device that is formed integrally with the dynamic reference frame member 256. One skilled in the art will understand that the tracking device 258 can be any appropriate device that can be an emitter, a receiver, a reflector, a sensor to sense a field, or any other appropriate device that can be tracked by a tracking system including a localizer.

The instrument 252 can be any appropriate instrument, for example and referred to herein as a catheter, electric lead, or stimulator. Other appropriate instruments can be used to deliver a therapy to a region of the anatomy or to record information from a region of the anatomy. For example, a recording device can be placed in a cranium 288 of the patient 204 to record electrical activity of a selected region of the brain for analysis and treatment options. Thus, it will be understood that the instrument 252 can be selected to be any appropriate device, and a stimulator, catheter, probe, etc. are merely exemplary.

The transmitter coil array 246 may also be supplemented or replaced with a mobile localizer 267. The mobile localizer 267 may be one such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. As is understood the localizer array can transmit signals that are received by the dynamic reference frame 254, and a tracking device 260. The dynamic reference frame 254 and the tracking device 260 can then transmit signals based upon the received signals from the array. One skilled in the art will also understand that the reverse can be true where the tracking device 206 will transmit a signal received by the array.

It will be understood that the tracking system may be any appropriate tracking system and can include an optical tracking system with an optical localizer 264, illustrated in phantom. Optical tracking systems can include the STEALTHSTATION® TRIA™ and STIMPILOT™, and electromagnetic systems can include the AXIEM™, all sold by Medtronic Navigation, Inc. of Louisville, Colo. Other tracking systems include acoustic, radiation, radar, infrared, laser, accelerometer, etc. The optical localizer 264 can transmit and receive, or combinations thereof. An optical tracking device 266 can be interconnected with the instrument 252, or other portions such as the dynamic reference frame 254. As is generally known the tracking device 266 can reflect or transmit an optical signal to the optical localizer 264 that can be used in the navigation system 200 to navigate or track various elements.

Further included in the navigation system 200 may be an isolator circuit or assembly 270. The isolator assembly 270 may be included in a transmission line to interrupt a line carrying a signal or a voltage to a navigation device interface 272. Alternatively, the isolator circuit included in the isolator assembly 270 may be included in the navigation device interface 272, the instrument 252, the dynamic reference frame 254, the transmission lines coupling the devices, or any other appropriate location. The isolator assembly 270 can isolate the patient from any of the instruments or portions that are in contact with the patient 204 should an undesirable electrical surge or voltage take place.

It should further be noted that the entire tracking system 244 or parts of the tracking system 244 may be incorporated into the imaging device 202, including the work station 229. Incorporating the tracking system 244 may provide an integrated imaging and tracking system. Any combination of these components may also be incorporated into the imaging system 202, which can include an appropriate imaging device.

The transmitter coil array 266 is shown attached to the receiving section 210 of the C-arm 206. It should be noted, however, that the transmitter coil array 266 may also be positioned at any other location as well. For example, the transmitter coil array 266 may be positioned at the X-ray source 208, within or atop an operating room (OR) table 276 positioned below the patient 204, on siderails associated with the OR table 276, or positioned on the patient 204 in proximity to the region being navigated, such as on the patient's chest. The coil array is used in an electromagnet tracking system as the localizer therefore. It will be understood by one skilled in the art that any appropriate localizer may be used.

The transmitter coil array 266 may also be positioned in the items being navigated, further discussed herein. The transmitter coil array 266 can include a plurality of coils that are each operable to generate distinct electromagnetic fields into the navigation region of the patient 204, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 266 is controlled or driven by the coil array controller 232. The coil array controller 232 drives each coil in the transmitter coil array 266 in a time division multiplex or a frequency division multiplex manner. In this regard, each coil may be driven separately at a distinct time or all of the coils may be driven simultaneously with each being driven by a different frequency. Upon driving the coils in the transmitter coil array 266, with the coil array controller 232, electromagnetic fields are generated within the patient 204 in the area where the medical procedure is being performed. The volume of the field relative to the patient or the patient in general can also be referred to as patient space. The electromagnetic fields generated in the patient space induce currents in a sensor 258 positioned on or in the device 252. These induced signals from the device 252 are delivered to the navigation device interface 272 through the isolation assembly 270 and subsequently forwarded to the coil array controller 232. The navigation device interface 272 may provide all the necessary electrical isolation for the navigation system 200. Alternatively, the electrical isolation may also be provided in the isolator assembly 270. Nevertheless, the isolator assembly 270 may be included in the navigation device interface 272 or may be integrated into the device 252, and any other appropriate location. The navigation device interface 272 can also include amplifiers, filters and buffers to directly interface with the tracking device 258 in the instrument 252. Alternatively, the instrument 252, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation device interface 272.

When the navigation system 200 uses an EM based tracking system, various portions of the navigation system 200, such as the instrument 252, the dynamic reference frame (DRF) 254, the instrument 252, are equipped with at least one, and generally multiple, EM tracking devices 260, that may also be referred to as localization sensors. The EM tracking devices 260 can include one or more coils that are operable with the EM localizer array 266 or 267. An alternative device may include an optical device, such as the optical tracking device 258a, and may be used in addition to or in place of the electromagnetic tracking device 258. The optical tracking device may work with the optional optical localizer 264. One skilled in the art will understand, however, that any appropriate tracking device can be used in the navigation system 200. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The EM tracking device 258 on the instrument 252 can be in a handle or inserter that interconnects with an attachment and may assist in placing an implant or in driving a portion. The instrument 252 can include a graspable or manipulable portion at a proximal end and the tracking device 258 may be fixed near the manipulable portion of the instrument 252 or at a distal working end, as discussed herein. The tracking device can also be positioned near a distal or working end of the instrument 252. In addition, the tracking device can be incorporated into the instrument 252, such as that disclosed in U.S. patent application Ser. No. 11/241,837 (now U.S. Patent Application Publication No. 2006/0084867) entitled, "Method and Apparatus for Surgical Navigation", filed Sep. 30, 2005, incorporated herein by reference. The tracking device 258 can include an electromagnetic device to sense the electromagnetic field generated by the transmitter coil array 266 that can induce a current in the electromagnetic device 258. Alternatively, it will be understood that the tracking device can transmit a signal to be received by the coil array.

The dynamic reference frame 254 of the tracking system 244 is also coupled to the navigation device interface 272 to forward the information to the coil array controller 232. The dynamic reference frame 254, according to various embodiments, may include a small magnetic field detector. The dynamic reference frame 254 may be fixed to the patient 204 adjacent to the region being navigated so that any movement of the patient 204 is detected as relative motion between the transmitter coil array 266 and the dynamic reference frame 254. The dynamic reference frame 254 can be interconnected with the patient in any appropriate manner, including those discussed herein. This relative motion is forwarded to the coil array controller 232, which updates registration correlation and maintains accurate navigation, further discussed herein. The dynamic reference frame 254 may be any appropriate tracking device used as the dynamic reference frame 254 in the navigation system 200. Therefore the dynamic reference frame 254 may also be optical, acoustic, etc. If the dynamic reference frame 254 is electromagnetic it can be configured as a pair, trio, etc. of orthogonally oriented coils, each having the same center or may be configured in any other non-coaxial or co-axial coil configurations.

The dynamic reference frame 254 may be affixed externally to the patient 204, adjacent to the region of navigation, such as on the patient's cranium 288, etc., as shown in FIG. 1. The dynamic reference frame 254 can be affixed to the patient's skin, by way of a selected adhesive patch and/or a tensioning system. The dynamic reference frame 254 may also be removably attachable to a fiducial marker 280. The fiducial markers can be anatomical landmarks or members attached or positioned on the patient's 204 body. The dynamic reference frame 254 can also be connected to a bone portion of the anatomy. The bone portion can be adjacent, the area of the procedure, the bone of the procedure, or any appropriate bone portion.

Briefly, the navigation system 200 operates as follows. The navigation system 200 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the device relative to the proposed trajectory and/or the determined anatomical target. The work station 229 in combination with the coil array controller 232 and the C-arm controller 218 can identify the corresponding point on the pre-acquired image or atlas model relative to the tracked device 252 and display the position on display 225. This identification is known as navigation or localization. An icon representing the localized point or instruments is shown on the display 225 within several two-dimensional image planes, as well as on three and four dimensional images and models.

To register the patient 204, a physician or user 282 may use point registration by selecting and storing particular points from the pre-acquired images and then touching the corresponding points on the patient's anatomy with a pointer probe or any appropriate tracked device, such as the instrument 252. The navigation system 200 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 280, such as anatomical or artificial landmarks. Again, the fiducial markers 280 are identifiable on the images and identifiable and accessible on the patient 204. The fiducial markers 280 can be artificial landmarks that are positioned on the patient 204 or anatomical landmarks that can be easily identified in the image data. The artificial fiducial markers 280, can also form part of the dynamic reference frame 254, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 280 rather than being the fiducial marker 280.

The system 200 may also perform registration using anatomic surface information or path information as is known in the art (and may be referred to as auto-registration). The system 200 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 200 continuously can track the position of the patient 204 during registration and navigation with the dynamic reference frame 254. This is because the patient 204, dynamic reference frame 254, and transmitter coil array 266 may all move during the procedure, even when this movement is not desired. Alternatively, the patient 204 may be held immobile once the registration has occurred, such as with a head frame. If the navigation system 200 did not track the position of the patient 204 or area of the anatomy, any patient movement after image acquisition would result in inaccurate navigation within that image. The dynamic reference frame 254 allows the tracking system 244 to track the anatomy and can assist in registration. Because the dynamic reference frame 254 is rigidly fixed to the patient 204, any movement of the anatomy or the transmitter coil array 266 is detected as the relative motion between the transmitter coil array 266 and the dynamic reference frame 254. This relative motion is communicated to the coil array controller 232, via the navigation probe interface 272, which updates the registration correlation to thereby maintain accurate navigation.

The dynamic reference frame 254 can be affixed to any appropriate portion of the patient 204, and can be used to register the patient to the image data, as discussed above. For example, when a procedure is being performed relative to the cranium 288, the dynamic reference frame 254 can be interconnected with the cranium 288. The dynamic reference frame 254 can be interconnected with the cranium 288 in any appropriate manner, such as those discussed herein according to various embodiments.

To enable navigation relative to image data, registration should occur and the navigation system 200 must be able to determine both the position of the patient's anatomy and the position of the instrument 252 or attachment member (e.g. tracking device 258) attached to the instrument 252. Knowing the location of these two items allows the navigation system 200 to compute and display the position of the instrument 252 or any portion thereof in relation to the patient 204 on the display device 225. The tracking system 244 is employed to track the instrument 252 and the anatomy simultaneously.

The tracking system 244, if it is using an electromagnetic tracking assembly, essentially works by positioning the transmitter coil array 266 adjacent to the patient space to generate a low-energy magnetic field generally referred to as a navigation field. Because every point in the navigation field or patient space is associated with a unique field strength, the electromagnetic tracking system 244 can determine the position of the instrument 252 by measuring the field strength at the tracking device 258 location. The dynamic reference frame 254 is fixed to the patient 204 to identify the location of the patient in the navigation field. The electromagnetic tracking system 244 continuously recomputes the relative position of the dynamic reference frame 254 and the instrument 252 during localization and relates this spatial information to patient registration data to enable image guidance of the instrument 252 within and/or relative to the patient 204.

To obtain a maximum reference it can be selected to fix the dynamic reference frame 254 in each of at least 6 degrees of freedom. Thus, the dynamic reference frame 254 or any of the tracking device 258 can be fixed relative to axial motion X, translational motion Y, rotational motion Z, yaw, pitch, and roll relative to the portion of the patient 204 to which it is attached. Any appropriate coordinate system can be used to describe the various degrees of freedom. Fixing the dynamic reference frame relative to the patient 204 in this manner can assist in maintaining maximum accuracy of the navigation system 200.

In addition the dynamic reference frame 254 can be affixed to the patient in such a manner that the tracking sensor portion thereof is immovable relative to the area of interest, such as the cranium 288. A head band may form a part of the dynamic reference frame 254. Further, a stereotactic frame, as generally known in the art, can be attached to the head band. Such systems for tracking and performing procedures are disclosed in U.S. patent application Ser. No. 10/651,267, filed on Aug. 28, 2003, now U.S. Pat. App. Pub. 2005/0049486, and incorporated herein by reference.

Although the navigation system 244, discussed above, can be provided in a plurality of ways and with a plurality of mechanisms it can be used to track the instrument 252. As discussed above the instrument 252 can be a catheter and can be any appropriate catheter and can include a tracking sensor such as the tracking device 258. Briefly, it will be understood that the catheter can represent any appropriate instrument such as a deep brain stimulator (DBS) lead, a needle, a probe, a guidewire, etc. The tracking device 258 included in the instrument 252 can be any appropriate tracking sensor and can be formed in any appropriate manner such as the catheters described in pending U.S. patent application Ser. No. 11/241,837, filed on Sep. 30, 2005, now U.S. Pat. App. Pub. No. 200610084867, incorporated herein by reference.

The instrument 252 can include the tracking device 258 at any appropriate position, such as near a distal end of the instrument 252. By positioning the tracking device 258 near the distal end of the instrument 252 knowing or determining a precise location of the distal end can be efficiently done. Determining a position of the distal end of the instrument 252 can be used to achieve various results, such as determining a precise position of the distal end of the instrument 252, a precise movement of the distal end of the instrument 252, or other appropriate purposes. It will be understood that knowing a position and moving the instrument 252 in a precise manner can be useful for various purposes, including those discussed further herein. Likewise, the instrument 252 can be directable or steerable according to various mechanisms and such as directing or pulling wires, directing or pulling signals, or any appropriate mechanism generally known in the art.

The instrument 252 can be used for various mechanisms and methods, such as delivering a material or therapy to a selected portion of the patient 204, such as within the cranium 288, peripheral muscles or nerves, the spinal cord, dorsal nerves, etc. The material or therapy can be a bioactive material, a pharmacological material, a contrast agent, an electrical current, or any appropriate material. The instrument 252 can also be provided to diagnose or assist in diagnosis For example, the instrument can include a micro-electrode recorder that can record or sense an electrical current in the patient 204. As discussed further herein, the instrument 252 can be precisely positioned via the navigation system 200 and otherwise used to achieve a protocol for positioning the material relative to the patient 204 in any appropriate manner, such as within the cranium 288. The instrument 252 may also include a brain probe to perform deep brain stimulation. The instrument 252 can be tracked to navigate it along the determined trajectory to stimulate an anatomical target, such as a fiber tract, axon, etc. in the patient 204.

As discussed above, the image data for the patient 204 can include any appropriate image data. For example, MRI image data can be obtained for selected portions of the anatomy. Further, the image data can be obtained at any appropriate time, such as prior to the performance of a procedure on the patient 204. Also, diffusion data regarding the patient can be obtained. Further, it will be understood that although a procedure on the cranium 288 and the brain is illustrated in FIG. 1, that any appropriate procedure can be performed.

Various types of image data can be obtained for different portions of the anatomy. As will be discussed further herein, anatomical data and functional data can be obtained for a selected region of the anatomy. Various types of data or information can include Diffusion Tensor Image (DTI) data, functional MRI data, etc. A hybrid image or an overlay image can be produced that displays both the anatomical data and the functional data at the same time. Alternatively, the functional data and the anatomical data can be displayed separately for viewing by the user 282.

The image data can be obtained at any appropriate time, such as preoperatively or intraoperatively. For example, the anatomical image data and the DTI can be obtained preoperatively. The image data, as discussed above, can then be registered to the patient 204 during the procedure according to various techniques. Therefore, the image data can be obtained at any appropriate time and can be used to both plan a procedure and to assist in the navigation of a surgical procedure.

Further, the image data can be used to assist in determining various functional and anatomical portions of the anatomy. For example, the DTI image data can be used to assist a user or a system to determine various selected regions of the anatomy. For example, the DTI analysis or development can be used to assist a user in determining the location, size, orientation, path, and the like of various axons or fiber tracts. The information can then used to assist in determining an appropriate target for a therapy. Determination of an appropriate tract or distinguishing a first fiber tract from a second fiber tract can be used to assist in both the navigation and planning of a procedure.

Figure 2:
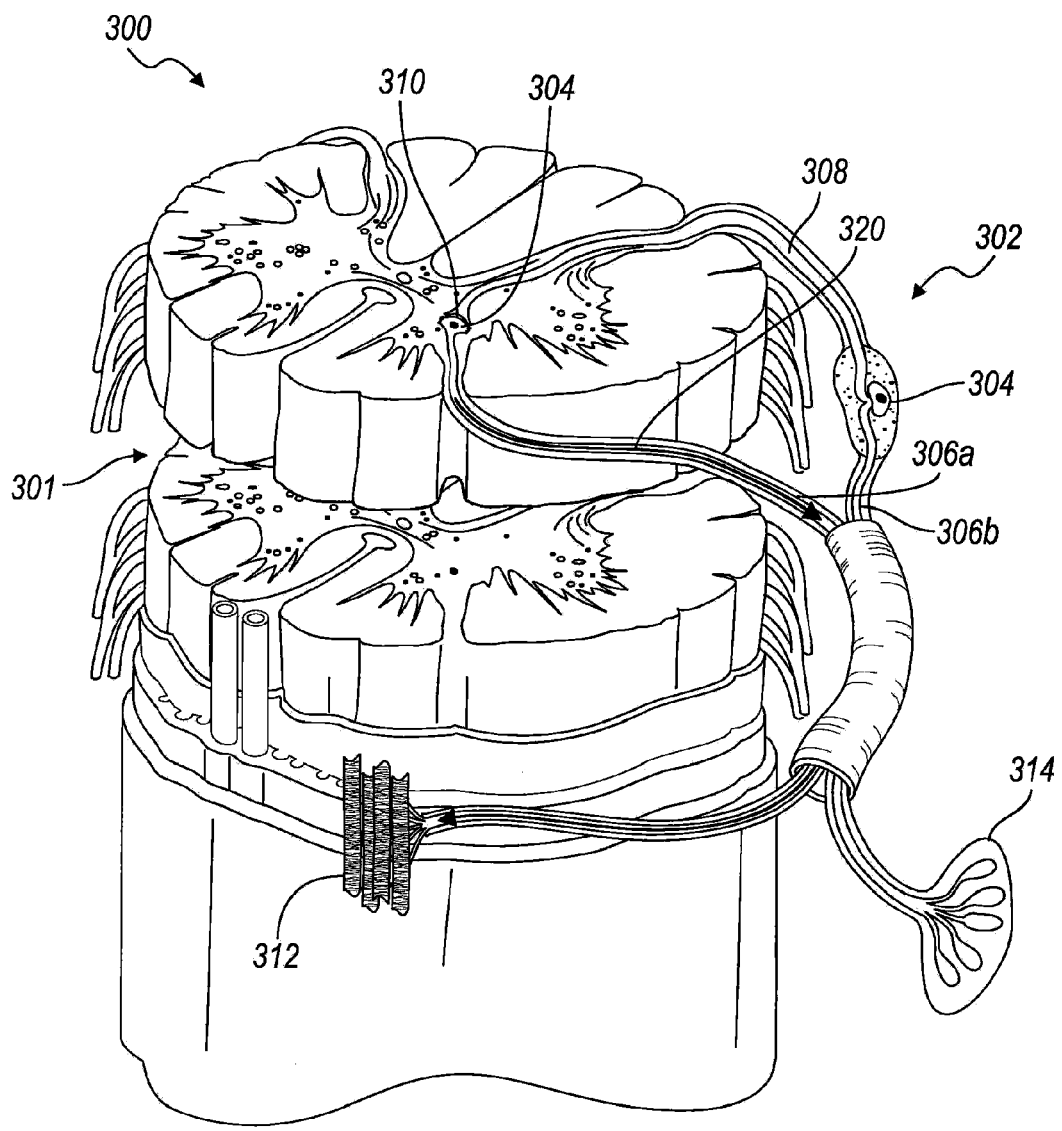
FIG. 2 is diagrammatic image data of a selected region of the anatomy including a spinal column and neurons relative thereto.
Figure 2A:
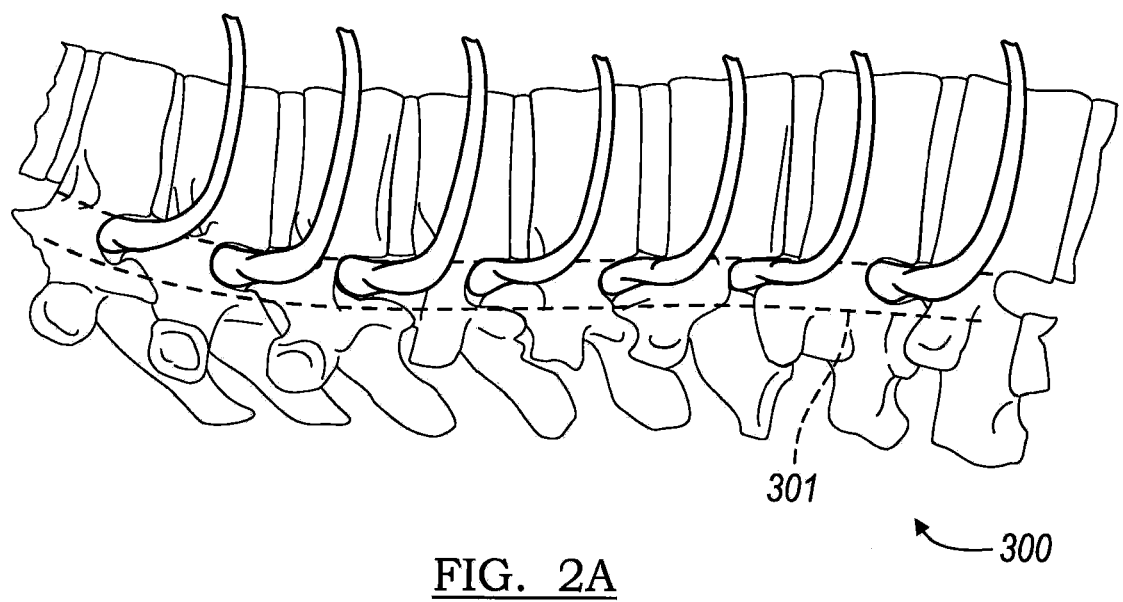
FIG. 2A is a diagram of a selected region of the anatomy including a spinal column and neurons relative thereto.

For example, with reference to FIGS. 2 and 2A, image data of a lower torso portion of the patient 204 can be imaged. For example, image data of a region of a spinal column 300 and in particular a spinal cord 301 can be imaged with the appropriate imaging system, such as a MRI. It will be understood that the representation in FIG. 2 is merely exemplary of information that can be obtained with an MRI. Nevertheless, MRI data can be used to display an appropriately dimensioned image, such as a two-dimensional, three-dimensional, or even four-dimensional image data of a selected portion of the anatomy, including the spinal column 300.

The image data can also include an image of one or more neurons 302. The neurons can be individual neurons or bundles of neurons. For example, various dorsal roots can be imaged and identified in the image data. DTI can be used to assist in identifying the various portions, such as the fiber tracts, in the image data.

The neurons 302, as understood in the art, can include various portions such as a cell body 304, an axon 306, and dendrites 308. It will be understood by one skilled in the art that various portions of the neuron 302 can also include other anatomical portions, such as myelin, other sheath portions, and the like. One skilled in the art will also understand that a signal can be transferred along the axon 306, past or across a synapse 310, and through the dendrite 308 to transfer information, such as a movement signal, a pain signal, or any other appropriate signal. For example, the signal can be transferred to a muscle fiber or bundle 312 or to an organ 314. The signal transfer can provide information to contract, expand, perform a function, transfer a pain signal, or the like.

As discussed above, in various conditions, an anomaly can occur, where selected signals are transferred without an anatomical purpose. For example, nerve damage or other damage can cause pain signals to be transferred for no apparent reason. Also, excessive activity can occur in a region of the anatomy that can be a source of issues in the anatomy. The signal can be transferred through the spinal column 300, including the dorsal column, to be interpreted by the brain in the cranium 288. Because of these anomalies, it may be selected to provide a treatment to the region to assist in reducing or eliminating the pain.

Treatments that can be applied can include stimulation of the neurons to assist in reducing the pain transferred to the brain to be interpreted or felt by the patient. The treatment can include treatment or stimulation of a single cell or fiber. The treatment can include providing an electrical signal or electrical current to assist in reducing a felt pain signal.

Magnetic resonance imaging can be used to impose a change on atoms that is interpreted by the magnetic resonance imager. Obtaining magnetic resonance image data is well understood in the art and will not be explained in detail here. Also, the magnetic resonance image data can generally be used to identify various anatomical portions, such as the cell body 304. In addition, the MRI data can include diffusion image data. The diffusion data can be used to determine a tensor to determine or illustrate a flow or movement of water. The flow of water can be generally understood to include diffusion of water.

Water can diffuse in various ways, such as isotropic or anisotropic. An anisotropic diffusion generally describes the movement of the water in a specific or selected direction or through a corridor or path. With the diffusion tensor data the, direction of the water can be determined and can be illustrated either separately or with the MRI image data. A processor, such as the planning processor 228 or the navigation processor 224, can be used to illustrate the diffusion tensor image data either alone or relative to an MRI data. The diffusion tensor data can include any appropriate illustration, such as a line 320.

The DTI data can be used for calculating, with the tensor, the main direction of diffusion of water in a region. Diffusion data can be analyzed for a particular portion of the image data, such as a voxel of image data, to determine the strongest direction of diffusion. When using 3-D data, such as MRI data, the diffusion direction can be determined in 3-D. To determine a path multiple voxels that touch one another are analyzed to determine a flow of water in a path from one point to another.

The line 320, either alone or with any appropriate image data, can be illustrated on the display 225. The image data can be used by a user to assist in determining a tract, such as an axon tract 306 or fiber tract in the imaged area of the patient 204. The axon tract 306 can constrict the movement of water. Therefore, the diffusion of water can be assumed or determined to be along the axon 306.

The determination of the axon 306 can be performed with any appropriate tractography method. It will be understood that an individual axon may not be determined or imaged, but rather a group of similarly oriented and positioned axons may be determined or imaged. The group of axons can be referred to as a fiber or neural tract. Therefore, a fiber tract can represent one or more axons that interconnect a group of cell bodies.

Generally, if diffusion occurs in an anisotropic manner then a tract is determined to be present. The tracts can be determined with various methods. For example, a fast marching or moving front method can be used to determine the diffusion of the water along the axon 306 to determine a tract. Once the entire diffusion tract has been determined, it can be used to assist in determining the location of a particular axon, such as an axon 306a to distinguish it from a second axon, such as the axon 306b. Therefore, the particular, or a particular, axon can be determined based on the collected image data.

The axon 306 of the neuron 302 is representative of a single neuron or a bundle of neurons in the patient 204. The neuron or bundle can also be physically dissected, if selected. The DTI, however, allows a graphical or visual or virtual dissection for analysis and treatment. The DTI analysis of the image data allows the determination of different neurons or bundles for treatment.

Treatment applied to the neurons can at any appropriate region, such as along the axon 306a. The axon 306a is more easily stimulated with electrical stimulation than other parts of the neuron, such as the cell body 304. Because the axon 306a is more excitable and a signal is generally transferred along the axon 306a, stimulating the axon 306a can increase efficiency of the stimulation and reduce the amount of current or voltage needed to achieve a selected stimulation to therapy result. Further, stimulating a particular axon, such as the axon 306a, can assist in reducing possible side affects that may occur when stimulating a general region of the neuron or stimulating an incorrect or additional axon (e.g. axon 306b) that is not part of the disease area. Also, stimulation of the axons or fiber tracts may produce a more robust therapeutic effect due to the convergence and/or density of information within the fiber tracts. This is opposed to stimulating a larger volume of cell bodies that send signals via the fiber tracts.

One skilled in the art will understand that stimulation of the selected neuron or bundle 302 can be applied to any appropriate location. Although stimulation of the axon 306a can provide a selected result, stimulation of the cell body 304, a combination of the cell body 304 and the axon 306a, stimulation within the grey matter, (i.e. near the synapse), stimulation of both the grey matter and the white matter, or any appropriate location can be applied. The image data of the anatomy that is obtained and the diffusion tensor analysis applied to the data can be used to identify the various portions of the neuron 302 or bundle of neurons. Therefore, an application of a treatment to a selected portion can be, enhanced or selected, based upon the determined portion of the neuron 302. Thus, the determination of the appropriate portions of the neuron or neuron bundle can be used to provide a selected treatment to the selected region. Thus, the stimulation can be applied anywhere along the neuron, such as near the affected region of the anatomy, such as an organ or a muscle, or substantially in or near the spinal cord 301.

The determination of the axon 306a, as distinguished from other axons or portions of the anatomy, such as the cell body 304 or muscle fiber 312, etc., can assist in providing a treatment to a particular area without affecting other areas of the anatomy. Also, if the treatment to be provided is stimulation stimulating the axon can affect a pathway or communication network within the patient 204. This can also increase the efficacy of a treatment, in addition to stimulating a more sensitive portion of the neuron. Further, as discussed above, the reduction of side affects may be obtained by eliminating or reducing the area to be stimulated with the instrument 252.

It will be understood that the instrument 252 can include a stimulator that can be used to stimulate the axon 306a and any appropriate portion of the anatomy, such as near the spinal column 300. It will also be understood that the instrument can include an implanted instrument, such as an implant and electrode, which is maintained near the axon 306a for continuous or extended stimulation thereof. The navigated instrument 252 can be any appropriate instrument or can be positioned at any appropriate location, and being positioned near the cranium 288 is merely exemplary.

Figure 3:
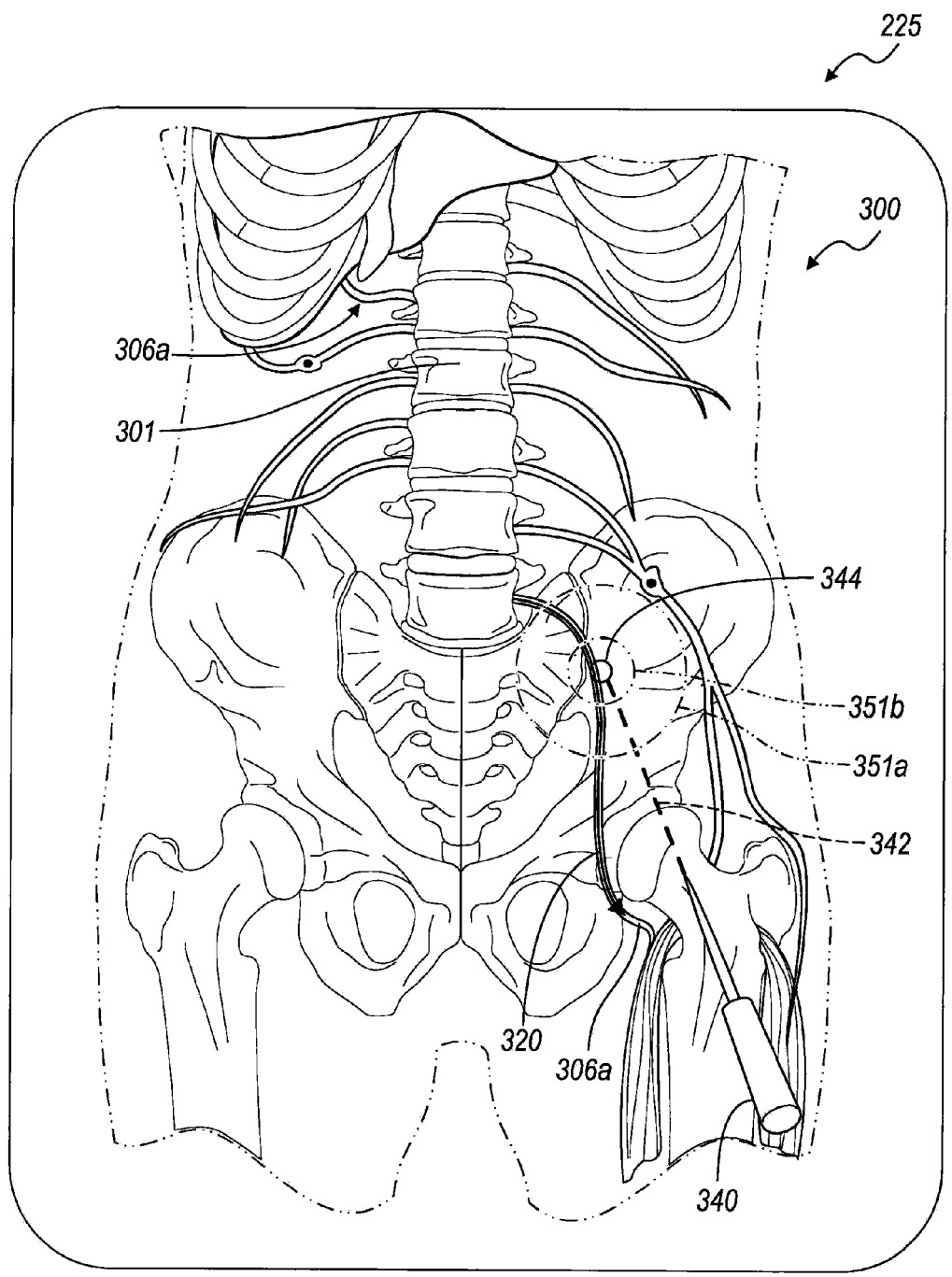
FIG. 3 illustrates a display displaying image data of a selected region of the anatomy according to various embodiments.

As illustrated in FIG. 3, the display 225 can illustrate any appropriate image data, such as MRI image data to illustrate the anatomy, including the spinal column 300 and the neuron 302. In the alternative, or in addition to the MRI or other anatomical image data, the DTI image data can also be displayed or superimposed over the MRI data on the display 225. As discussed above, the DTI image data can include the line 320 that illustrates the diffusion path and direction of water or fluid through a selected portion of the anatomy. One skilled in the art will understand, the diffusion of the water along the path can illustrate or be used to determine the axon or location of the axon 306a. It will also be understood that the axon 306a, as determined by any appropriate means, including the DTI image data 320, can be determined or selected to be the axon to be stimulated.

The instrument 252 can be displayed on the display 225 in any appropriate manner, such as superimposing an icon 340 representing the instrument 252 or the MRI/DTI image data using the navigation processor 224 or any appropriate system, including the tracking system 244. As discussed above, the instrument 252 can be tracked in any appropriate manner and with the appropriate tracking system. Nevertheless, on the display 225, the various icons can be used to illustrate the position, planned position, or the like of the instrument 252.

On the display 225, the icon 340 can illustrate a current location of the instrument 252 relative to the image data, if an image guided system is selected. In addition to the current location icon 340, a planned or projected location icon 342 can also be displayed. The projected location icon 342 can include a planned trajectory of the instrument 252 to reach a target location 344. The target location 344 can be determined at any appropriate time such as during pre-operative planning or intra-operative planning. The target location 344, which can include an anatomical target, can be determined or selected based upon the various information including the DTI information 320. The projected icon 342 can act as a guide for the user 282 to move the instrument 252 relative to the selected axon 306a.

As discussed above, the instrument 252 can be any appropriate instrument such as a stimulator to stimulate the axon 306a. The navigation of the instrument 252 can assist in positioning the instrument at a selected location, such as the target location 344 illustrated on the display 225. The target location 344 can be determined in any appropriate manner, such as automatically based upon the DTI information 320, manually by the user, or any combination thereof.

The target location 344 can be displayed with the icon 340 on the display 225. Additional information can also be provided to the user 282 to let the user know when the target location has been reached, assist the user in reaching the target location with the instrument 252, or any appropriate information. Further, the target location 344, as discussed above, can be based upon selected information and the information can also be displayed on the display 225 with the progress information. Therefore, the use of selected information, such as the DTI information 320, can be used to assist in navigating the instrument 252 relative to the patient 204.

As discussed above, an appropriate therapy can be applied to a selected region, such as the axon 306a. Any selected area or combination of areas can be treated. Further, the target icon 344 can be used to indicate a selected location for the application of a therapy. In addition to the target icon 344, additional information can also be displayed on the display 225, which can include an "affected area". An affected area can include a first affected area 351a and a second affected area 351b.

The affected area icons 351a, 351b can illustrate the areas that would be affected by a particular treatment and/or an amount of the treatment or therapy. For example, if the instrument 252 is a stimulation probe, the affected area icons 351a, 351b can be used to illustrate the area that would be stimulated by a selected electrical current over a period of time. The affected area icons 351a, 351b can also illustrate the area that a particular therapy would spread over a selected period of time. Therefore, the affected area icons 351a, 351b can assist a user 282 in determining an appropriate amount of a therapy to be applied and where the therapy might be effective. Also, the type or amount of treatment can be selected intraoperatively, thus the icons can change intraoperatively.

The affected area icons 351a, 351b can also assist a user in reducing selected side effects. As discussed above, the identification of the particular axon or fiber tract 306a, as distinguished from the second fiber tract 306b can be useful in limiting side effects to un-diseased areas. Therefore, the affected area icons 351a, 351b can also assist a user in determining the amount of a therapy that should be applied to maximize the therapy applied to the selected axon 306a, while minimizing the effects of the therapy on an unselected axon, such as the axon 306b. Thus, the display 225, or any appropriate information output, can be used with the user to determine an appropriate affected area of a therapy.

One skilled in the art will understand that any appropriate target location can be determined or selected, and the selection of the axon 306a is merely exemplary. Nevertheless, locating the axon 306a can be assisted or enhanced with the DTI icon 320. As discussed above, the DTI data can assist in determining the location of the axon 306a, which can be determined or selected for a treatment or therapy. Further, the combination of the DTI icon 320 with other appropriate information, such as anatomical MRI information, can further assist in the determination of the location of a selected region to be treated. The treatment of the axon 306a can be any appropriate treatment such as stimulation with a DBS probe, ablation, cutting, or the like.

Figure 4:
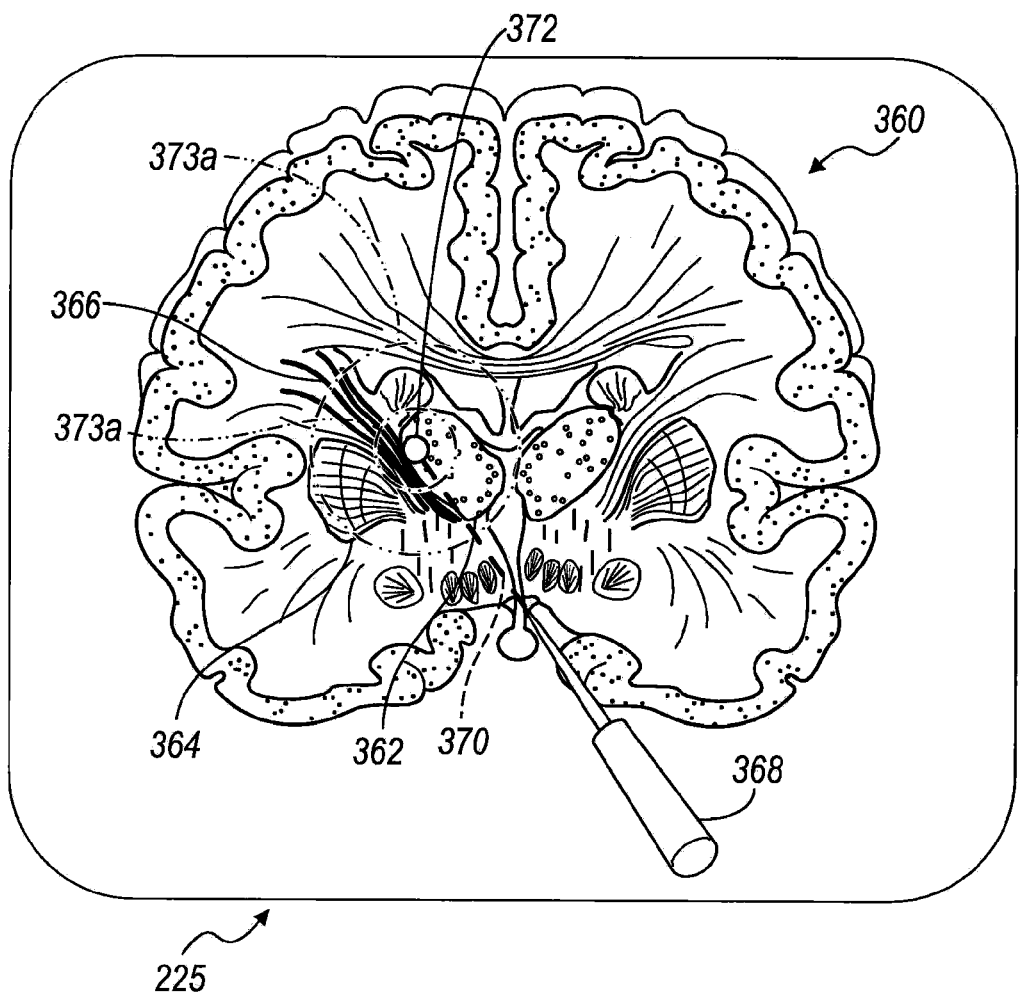
FIG. 4 illustrates a display displaying image data of a selected region of the anatomy according to various embodiments.

With reference to FIG. 4, the procedure also can be provided or applied to the brain. The patient 204 can be imaged in any appropriate manner, such as those discussed above. For example, MRI image data can be obtained of the brain and the images or the image data of the brain can be displayed as an image 360 on the display 225. The MRI image data can generally display or show the anatomy of the brain. In addition, DTI data can also be obtained for the brain region. The DTI data can be obtained in substantially similar ways as that discussed above, and can also be displayed on the display 225. The DTI data or information can include tensor analysis of diffusion data.

The DTI data can be displayed in any appropriate manner, such as a line or a series of lines 362. The line 362 can show the diffusion direction and the diffusion amount within the data, as obtained and generally understood in the art. Therefore, the DTI data can be interpreted to display or show a tract between various regions in the brain. For example, the tract or fiber connection or axon connection can be amongst the basal ganglia, such as between the lenticular nucleus 364 and the caudate nucleus 366. Therefore, the DTI data can be used to determine a connection or communication region, such as along an axon, between various portions of the brain. It will be understood that within the brain connection paths or tracts are formed of axons and synapses between axons. The connection paths or tracts can be between different neuron cell bodies and neuron concentrations in the brain.

The DTI data can be obtained at any time, such as substantially with the MRI data. Therefore, the DTI data can be displayed substantially simultaneously or can be analyzed and overlaid on the MRI image data for display on the display 225. It will also be understood that these various types of data can be displayed separately and displaying them together or overlaying one on top of another is merely exemplary.

Further, on the display, an icon 368 representing a current location of the instrument 225 can be illustrated. A proposed or projected icon 370 can also be illustrated on display to show a proposed or projected movement or position of the instrument 252. As discussed above, the projected icon 370 can include either a proposed or planned path of the instrument 252 or a projected position of the instrument 252, if it continues along its current path. As discussed above, the determination of a position of the instrument is performed by the tracking system 244, which can be any appropriate tracking system. The display 225 can also display a target icon 372.

The target icon 372 can be generally near an axon or one of the determined tracks within the brain. The tract and target can be determined based upon the DTI data and other image data obtained of the patient 240. As discussed above the tract icon 362 can be a display of the DTI data for the region of the brain and the target icon 372 can be selected in any appropriate manner. Further, the tract icon 362 can be augmented or enhanced in any appropriate manner such as with color, arrows, moving icons, or the like.

With continuing reference to FIG. 4, affected area icons 373a, 373b can also be illustrated on the display 225. The affected area icons 373a, 373b can illustrate an area that would be affected by a selected treatment if applied at certain parameters. This can assist in ensuring that a therapy is applied only to a selected region or a selected axon, such as the fiber tract, illustrated by icon 362. The various side effects can also be reduced by ensuring that the therapy would only affect the selected region.

The DTI data can be used to identify and determine the tracts near which the instrument 252 can be positioned. The instrument 252 can be any appropriate instrument such as an ablation device, a stimulator, an electrode, a probe, or the like. The instrument 252 can also include a permanent or long-term implant or a single use or short-term implant. Nevertheless, positioning of the instrument 252 near the axon, which can be determined by the DTI data 362, can assist in ensuring an appropriate or selected positioning of the instrument 252.

One skilled in the art will understand that the image data and the DTI data illustrated in FIG. 4 are merely exemplary. Various different and numerous tracts can be determined and identified with the DTI data. The tracts can be displayed with or without other image data and be used by a user in a selected manner.

In addition to the tracts discussed above, other tracts can be determined. As schematically illustrated in FIG. 5 various portions of the brain can be identified in MRI image data, For example the thalamus 400, the globus pallidus interna 402, sub-thalamic nucleus 404, the zona incerta (ZI) 406, and the pedunculopontine nucleus (PPN) 408 can be identified in selected MRI image data. These portions of the brain can be identified in any appropriate manner and selected procedures can be carried out on them or near them. It can be selected however, to identify the axons or tracts that interconnect them. These tracts, which allow for communication between these regions, can then have a therapy applied to them.

The tracts between the various regions can include an ansa lenticularis 412, an internal capsule 414, a lenticular fasciculus 416, and Fields of Forel 418, 420. The tracts can allow for communication and stimulus transport between the different regions of the brain. These tracts can also be stimulated with stimulators and probes. The tracts can be identified with the DTI data similar to the DTI data 362. Though various tracts can be identified for different procedures or treatments the use of the DTI data can assist in the appropriate identification.

As briefly discussed above, image data, such as MRI diffusion image data can be used to perform a tensor analysis to provide for a virtual or in vivo dissection of the anatomy. The virtual dissection can identify various fiber tracts and axon tracts within the anatomy, such as the brain. For example, the brain can include long and short fibers that interconnect various regions of the brain, as discussed above. Further exemplary regions can include the interior limb of the internal capsule. Various mood disorders, such as depression, manic, and the like can be treated by a stimulating the anterior limb of the internal capsule. Further fiber tracts, in the brain, include the mammillothalamic tract. The mammillothalamic tract can be targeted for epilepsy. Stimulation can include electrical stimulation, such as providing a current through a probe or electrode to the selected region of the anatomy. The fiber tracts can be identified with the DTI data and stimulating the fiber tracts can be performed.

It will be understood that a combination of any appropriate anatomical features can be stimulated, however. For example, the white matter and grey matter can be stimulated together, separately, in sequence or one or the other can be stimulated. Nevertheless, the DTI data can be used in combination with other image data to assist in identifying the particular fiber tracts to allow for stimulation thereof or in areas relative thereto.

With reference to FIG. 6, additional peripheral nerves can be identified. A display can be used to display image data of a selected portion of the patient 204. On the display, image data can be displayed as can DTI data 370. As illustrated above, the DTI data 370 can be used to identify tracts of the various nerves or nerve tracts. The nerves can include the peripheral nerves that extend from the spinal cord into various regions of the anatomy, such as over the cranium. Stimulation of the nerves of the nerve tracts can be used to treat various issues such as head pain or headaches. Specific nerve tracts can include those of the occipital nerves.

Therefore, one skilled in the art will understand that the provision of stimulation to nerve tracts or fiber tracts need not be deep within an anatomical structure, such as the brain, and can be near the surface. In addition to the peripheral nerves, which can surround the cranium, peripheral nerves that extend from the spinal cord can also be stimulated, to treat pain in the anatomy or treat various ailments of selected organs.

Stimulation of the selected portions of the anatomy can be provided for various purposes. The identification and isolation of the axon fiber tracts, such as within the image data, can be used to assist in identifying regions for stimulation or treatment. It will be understood that various techniques can be used to identify the axons and DTI image data is merely exemplary. The DTI image data can assist in resolving or identifying specific tracts, but analysis of the image data can use other techniques to identify axon tracts. For example, a user can review the image data displayed and identify specific or selected axon fiber tracts for positioning a treatment device.

Further, identifying the fiber tracts or axons of neurons can assist in positioning treatment or a treatment device, such as the instrument 252, relative thereto. Positioning the instrument directly on or only near the axons, however, is not required. A selected position to provide a treatment can overlap both the axon and a cell body, and other portions of the anatomy. For example, such as within the brain, stimulation of both the fiber tract (white matter) and cell bodies or other portions of the brain (grey matter) can be selected to provide a treatment. Therefore, providing a treatment only to the axon is not required.

One skilled in the art will understand that the image data, including the MRI and the DTI, can be obtained at any time. Thus, the data can be obtained prior to a procedure to assist in planning a procedure. The target can be identified, which can include the tract that is determined with the DTI data. Further, a projected or planned trajectory can be determined while planning the procedure.

The data can also be used for display during a procedure to assist in navigation of the instrument 252 to the selected target. The target can be selected intra-operatively or pre-operatively. In any case, the target can be identified as an axon with the DTI data. The instrument, which can include a stimulator, can then be navigated to the target for performing the procedure.

Various issues can be treated with a stimulator. For example various psychiatric issues can be treated with stimulation, such as Obsessive Compulsive Disorder and depression. Stimulation of the tracts can provide additional stimulation in the selected portion of the brain to treat these issues. Also, epilepsy and Parkinson's disease can be treated by stimulating selected regions in the brain.

Stimulating the tracts directly can also assist in reducing power or current usage and increase efficiency and reduce side effects of a stimulation procedure. Thus, the determination of the tracts can assist in directing a stimulation directly to the tract. The DTI data can assist in determining the tract by identifying the regions in which anisotropic diffusion is occurring.

As discussed above the tracts can be more sensitive to stimulation, thus a lower current can be used when treating the tract. Also, the area being stimulated can be more definitely or narrowly determined, which can also allow for reduction of current during stimulation. Side effects can also be reduced by limiting the current and the areas to be stimulated. Thus, stimulating the tracts determined with the DTI data can assist in increasing the efficiency and efficacy of the procedure.

One skilled in the art will also understand that any appropriate tracts throughout the body can be determined and stimulated. Tracts in the brain and spinal column are merely exemplary of tracts to be stimulated. Other tracts, as discussed above can include peripheral nerve tracts. Also, any appropriate instrument can be navigated relative to the selected or determined areas to provide any appropriate treatment to the selected area or target.

As discussed above, the application of a therapy to a particular region can be enhanced by determining a fiber tract or axon that transmits signals between selected anatomical regions. The axon can be treated with any appropriate treatment, such as an electrical stimulation to achieve a selected result. The axons or fiber tracts can be determined with various techniques, such as DTI image data that can be used with or without anatomical image data. Thus, the use of the DTI image data can assist a user in determining a particular fiber tract. It also can assist a user in determining a first particular fiber tract from a second particular fiber tract for application of therapy to the particular fiber tract. In addition, the fiber tract can be mapped appropriately with the DTI data and image data for application of therapy to a selected location on the fiber tract or to multiple locations on the fiber tract.

The identification of a fiber tract for application of a therapy can assist in reducing an amount of current applied during stimulation and enhance accuracy of the application of the therapy. As opposed to applying a therapy to a general area, such as to the sub-thalamic nucleus or the basal ganglia, the DTI image data can assist in determining a particular fiber tract to which a therapy can be applied.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A method of performing a procedure on a selected portion of an anatomy, comprising:
   accessing image data of the selected portion of the anatomy;
   accessing a second source of data relating to the selected portion of the anatomy;
   analyzing the second source of data;
   identifying a fiber tract in the accessed image data based on the analyses of the second source of data;
   determining a selected position of treatment in the anatomy based on the accessed image data and the identified fiber tract to initially and directly affect the identified fiber tract with a treatment;
   providing an output from a processor to display a target icon on a display device superimposed on the accessed image data to illustrate the selected position in the anatomy;
   determining a location of an instrument with the processor via tracking a tracking device associated with the instrument by interaction with a localizer of a tracking system;
   providing an output from the processor to display an instrument icon superimposed on the accessed image data on the display based upon the determined location;
   moving and navigating the instrument to the selected position of treatment identified by the superimposed target icon, further comprising,
      executing instructions with the processor to plan at least a portion of a planned trajectory;
      superimposing a planned trajectory icon on the accessed image data relative to the superimposed target icon on the display device illustrating the planned trajectory; and
      updating the display to illustrate the determined location of the instrument as the instrument icon representing the location of the instrument relative to the target icon and the planned trajectory icon; and
   applying a treatment to the selected position in the anatomy with the instrument to efficiently affect the fiber tract after the instrument reaches the selected position illustrated by the target icon that is superimposed on or adjacent to a portion of the accessed image data, wherein the fiber tract includes at least an axon.

2. The method of claim 1, wherein accessing imaging data includes with an imaging system at least one of accessing magnetic resonance image data, accessing x-ray image data, accessing computer aided tomography image data, accessing PET image data, accessing ultrasound image data, accessing SPECT image data, or combinations thereof.

3. The method of claim 1, wherein accessing a second source of data includes accessing diffusion data of a material in the anatomy.

4. The method of claim 3, wherein accessing the image data of the anatomy and accessing the diffusion data of the anatomy occurs substantially simultaneously.

5. The method of claim 3, wherein analyzing the second source of data includes determining a diffusion direction of the material diffused in the anatomy.

6. The method of claim 5, further comprising:
   superimposing a fiber tract icon representing the identified fiber tract onto the obtained image data at the selected position of the anatomy.

7. The method of claim 6, wherein the fiber tract icon includes at least one of a line, an arrow, a plurality of lines, or combinations thereof.

8. The method of claim 1, wherein determining a selected position includes selecting at least one of an intracranial fiber tract, a dorsal fiber tract, a peripheral nerve fiber tract, an axon, a cell body, a dendrite, or combinations thereof and selecting the identified fiber tract to apply the therapy initially and directly.

9. The method of claim 1, wherein applying a treatment to the selected position includes applying an electrical current, a chemical therapy, a biological therapy, a radiation therapy, an implant, or combinations thereof.

10. The method of claim 1, wherein determining the selected position consists of determining a location of a peripheral nerve tract.

11. A method for performing a surgical procedure on an anatomy, comprising:
    obtaining data regarding the anatomy;
    analyzing the obtained data;
    selecting an identified fiber tract in the anatomy based upon the analyzed obtained data to apply a selected therapy, wherein the selected therapy includes applying stimulation to a fiber tract within the anatomy;
    executing instructions with a processor to determine a target location relative to the selected and identified fiber tract where the selected therapy is operable to be efficiently applied to directly affect the selected and identified fiber tract; and
    displaying:
       a target location icon representing the determined target location on a display device;
       an instrument icon representing a navigated instrument relative to the anatomy and the selected and identified fiber tract at least by viewing the display; and
    wherein the selected therapy is applied with the instrument that has been navigated relative to the anatomy and the selected identified fiber tract as illustrated with the instrument icon relative to the displayed target icon to stimulate the selected identified fiber tract.

12. The method of claim 11, wherein the obtained data includes at least one of image data, diffusion data, or combinations thereof.

13. The method of claim 12, wherein analyzing the obtained data includes determining a diffusion tensor of the diffusion data.

14. The method of claim 13, wherein selecting the identified a fiber tract includes determining and identifying the fiber tract based upon the diffusion tensor.

15. The method of claim 14, further comprising:
    planning a path to the target location;
    displaying a path icon representing the planned path to the target location near the selected fiber tract;
    wherein navigating the instrument includes tracking the instrument with a tracking system relative to the anatomy and determining the location of the instrument relative to the target location and the planned path and displaying an instrument icon representing the tracked location of the instrument.

16. The method of claim 15, further comprising:
    displaying on the display device a fiber tract icon representing the selected and identified fiber tract of the anatomy and the target location icon near or at the fiber tract icon.

17. The method of claim 16, further comprising:
obtaining image data of the region of the anatomy; and
superimposing on the image data at least one of the instrument icon, the fiber tract icon, the planned path icon, or combinations thereof.

18. The method of claim 15,
wherein planning the path includes determining, with a processor, a plan path for moving the instrument to the target location;
wherein navigating the instrument to the selected position of treatment, further comprises:
superimposing the path icon on the displayed image data representing the plan path relative to the superimposed target icon on a display device; and
updating the display to illustrate the determined position of the instrument as the instrument icon relative to the target location icon and the path icon.

19. The method of claim 15, further comprising executing instructions with the processor to generate a signal to display an icon illustrating a forward projected path of the instrument based on the current tracked location of the instrument.

20. The method of claim 11, wherein identifying a region of the anatomy relative to the identified fiber tract includes identifying at least one of a cell body, a neurological feature, a ganglia, a dorsal fiber tract, a synapse, or combinations thereof.

21. The method of claim 11, wherein the selected therapy includes an electrical current, applying a radiation, applying a thermal energy, and combinations thereof.

22. The method of claim 11, further comprising:
wherein selecting the fiber tract relative to a selected region of the anatomy includes identifying a peripheral nerve tract;
wherein applying a therapy includes applying an electrical stimulation to the fiber tract.

23. The method of claim 11, wherein selecting a fiber tract includes identifying a fiber tract in a brain, a fiber tract in a spinal column, a fiber tract in a peripheral nerve, or combinations thereof.

24. A method for performing a surgical procedure on an anatomy, comprising:
operating a processor system, including:
obtaining image data of a selected portion of the anatomy;
obtaining a diffusion tensor data relating to the selected portion of the anatomy;
analyzing the diffusion tensor data;
identifying a fiber tracts in the obtained image data at least in part with the analyses of the diffusion tensor data;
selecting at least one of the identified fiber tracts;
determining a target location near the selected fiber tract so that a selected therapy is to initially affect the selected fiber tract and where the selected therapy is operable to be efficiently applied to directly affect the selected fiber tract, and
displaying a target location icon representing the determined target location on a display device;
navigating an instrument relative to the anatomy and the selected fiber tract at least by viewing the display for applying the selected therapy with the instrument that has been navigated relative to the anatomy and the selected fiber tract to stimulate the selected fiber tract; and
applying the selected therapy by stimulating the selected fiber tract within the selected portion of the anatomy.

25. The method of claim 24, wherein navigating the instrument further comprises:
determining a location of the instrument via tracking a tracking device by interaction with a localizer of a tracking system;
providing an output from the processor to display an instrument icon superimposed on the obtained image data on the display; and
moving the instrument to the selected position of treatment identified by the superimposed target location icon.

26. The method of claim 25, wherein navigating the instrument further comprises,
executing instructions with the processor to plan at least a portion of the procedure;
superimposing a planned trajectory icon on the image data relative to the superimposed target location icon on the display device illustrating the plan of at least a portion of the procedure; and
updating the display to illustrate movement of the instrument with the instrument icon representing the location of the instrument as the instrument is moved relative to the target icon and the planned trajectory icon.

27. The method of claim 26, wherein the superimposed target location icon is on or adjacent to a portion of the image data representing an axon, and wherein applying the selected therapy is applying the selected therapy to the axon.

28. The method of claim 26, further comprising:
selecting the instrument to be at least one of a stimulation probe, an ablation device, an electrical lead, an electrical recorder, or combinations thereof.

29. The method of claim 26, further comprising:
executing instructions with the processor to provide an output to the display device to display a treatment affect area as a treatment icon on the display device while applying the selected therapy or immediately prior to applying the selected therapy to illustrate a predicted therapy region.

30. The method of claim 29, wherein executing the instructions with the processor to provide an output to the display device includes providing an output to the display device to change intraoperatively the treatment icon to show effects of the selected therapy.

* * * * *

UNITED STATES PATENT AND TRADEMARK OFFICE
CERTIFICATE OF CORRECTION

| | | |
|---|---|---|
| PATENT NO. | : 8,532,741 B2 | Page 1 of 1 |
| APPLICATION NO. | : 11/683695 | |
| DATED | : September 10, 2013 | |
| INVENTOR(S) | : Heruth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1318 days.

Signed and Sealed this
Seventeenth Day of March, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,532,741 B2 | Page 1 of 1 |
| APPLICATION NO. | : 11/683695 | |
| DATED | : September 10, 2013 | |
| INVENTOR(S) | : Gabriela C. Molnar | |

It is certified that error appears in the above-identified patent and that said Letters Patent is hereby corrected as shown below:

In the Claims

Column 24, lines 2-3, claim 24: "device; navigating" should read -- device; and navigating --.

Signed and Sealed this
Eighth Day of September, 2015

Michelle K. Lee
*Director of the United States Patent and Trademark Office*